United States Patent
Bunker et al.

(10) Patent No.: US 10,507,167 B1
(45) Date of Patent: Dec. 17, 2019

(54) SMART PILL BOX AND MEDICAL COMPLIANCE MONITORING

(71) Applicant: Vivint, Inc., Provo, UT (US)

(72) Inventors: Brandon Bunker, Highland, UT (US); Rongbin Lanny Lin, Draper, UT (US); Harrison Taylor Jenkins, Salt Lake City, UT (US)

(73) Assignee: Vivint, Inc., Provo, UT (US)

( * ) Notice: Subject to any disclaimer, the term of this patent is extended or adjusted under 35 U.S.C. 154(b) by 0 days.

(21) Appl. No.: 16/036,802

(22) Filed: Jul. 16, 2018

Related U.S. Application Data

(63) Continuation of application No. 15/468,086, filed on Mar. 23, 2017, now Pat. No. 10,022,305, which is a continuation of application No. 14/543,260, filed on Nov. 17, 2014, now Pat. No. 9,603,776.

(51) Int. Cl.
*A61J 7/04* (2006.01)

(52) U.S. Cl.
CPC ........... *A61J 7/0427* (2015.05); *A61J 7/0436* (2015.05); *A61J 7/0454* (2015.05)

(58) Field of Classification Search
CPC ........................ G08B 21/0202; G08B 21/0297; G08B 21/04; G08B 23/00; G06F 19/4562; A61J 7/0427; A61J 7/0436; A61J 7/0454; A61J 7/048; A61J 7/04; A61B 5/002; A61B 5/0024; A61B 5/02

See application file for complete search history.

(56) References Cited

U.S. PATENT DOCUMENTS

| | | | |
|---|---|---|---|
| 5,983,193 A | 11/1999 | Heinonen et al. | |
| 7,956,727 B2 | 6/2011 | Loncar | |
| 8,085,135 B2 | 12/2011 | Cohen Alloro et al. | |
| 8,224,667 B1 | 7/2012 | Miller et al. | |
| 8,487,758 B2 | 7/2013 | Istoc | |
| 9,361,778 B1 | 6/2016 | German | |
| 9,443,062 B2 * | 9/2016 | Long | G06F 19/3462 |
| 9,603,776 B2 * | 3/2017 | Bunker | A61J 7/0084 |
| 10,022,305 B2 * | 7/2018 | Bunker | A61J 7/0084 |
| 2003/0221687 A1 | 12/2003 | Kaigler | |
| 2007/0174092 A1 | 7/2007 | Lara et al. | |
| 2007/0186923 A1 * | 8/2007 | Poutiatine | A61J 7/0038 128/200.14 |

(Continued)

FOREIGN PATENT DOCUMENTS

| | | |
|---|---|---|
| WO | 2009156832 A1 | 12/2009 |
| WO | 2011054000 A1 | 5/2011 |

*Primary Examiner* — Van T Trieu
(74) *Attorney, Agent, or Firm* — Holland & Hart, LLP

(57) ABSTRACT

Methods and systems are described for monitoring medication use with a home automation system. An example medication monitoring system includes a medication storage device, a proximity device, and a dispenser module. The medication storage device is configured to hold a plurality of medications. The proximity device is configured to detect an activity of a user relative to the medication storage device. The dispense module is configured to detect a pattern of the activity based on data received from the proximity device, and generate a notice. The notice may be generated if the pattern is broken. The notice may include a summary report on usage of the medication storage device. The notice may include an alarm if the medication storage device is, for example, tampered with or moved.

13 Claims, 13 Drawing Sheets

(56) References Cited

U.S. PATENT DOCUMENTS

| | | |
|---|---|---|
| 2008/0111685 A1 | 5/2008 | Olson et al. |
| 2008/0149659 A1 | 6/2008 | Dishongh et al. |
| 2011/0169635 A1 | 7/2011 | Johnson |
| 2012/0330684 A1 | 12/2012 | Jacobs et al. |
| 2013/0096953 A1 | 4/2013 | Beverly et al. |
| 2013/0131586 A1 | 5/2013 | Poutiatine et al. |
| 2013/0268292 A1 | 10/2013 | Kim et al. |
| 2014/0335490 A1 | 11/2014 | Baarman et al. |
| 2015/0305653 A1 | 10/2015 | Gallagher |
| 2015/0347713 A1 | 12/2015 | Seeger |
| 2016/0005300 A1 | 1/2016 | Laufer et al. |

\* cited by examiner

SMART PILL BOX AND MEDICAL COMPLIANCE MONITORING

CROSS-REFERENCE TO RELATED APPLICATIONS

The present application is a continuation of U.S. patent application Ser. No. 15/468,086, titled: "Smart Pill Box and Medical Compliance Monitoring," filed Mar. 23, 2017, now U.S. Pat. No. 10,022,305, issued on Jul. 28, 2018 which is a continuation of U.S. patent application Ser. No. 14/543,260, titled: "Smart Pill Box and Medical Compliance Monitoring," filed Nov. 17, 2014, now U.S. Pat. No. 9,603,776, issued on Mar. 28, 2017, the disclosures of which are incorporated by reference herein in their entirety.

BACKGROUND

Advancements in media delivery systems and media-related technologies continue to increase at a rapid pace. Increasing demand for media has influenced the advances made to media-related technologies. Computer systems have increasingly become an integral part of the media-related technologies. Computer systems may be used to carry out several media-related functions. The wide-spread access to media has been accelerated by the increased use of computer networks, including the Internet and cloud networking.

Many homes and businesses use one or more computer networks to generate, deliver, and receive data and information between the various computers connected to computer networks. Users of computer technologies continue to demand increased access to information and an increase in the efficiency of these technologies. Improving the efficiency of computer technologies is desirable to those who use and rely on computers.

With the wide-spread use of computers and mobile devices has come an increased presence of home automation and security products. Advancements in mobile devices allow users to monitor and/or control an aspect of a home or business. As home automation and security products expand to encompass other systems and functionality in the home, opportunities exist for further monitoring occupant activities in the home, particularly activities associated with health and well-being aspects of occupants.

SUMMARY

Methods and systems are described for monitoring medication use with a home automation system. An example medication monitoring system includes a medication storage device, a proximity device, and a dispenser module. The medication storage device is configured to hold a plurality of medications. The proximity device is configured to detect an activity of a user relative to the medication storage device. The dispense module is configured to detect a pattern of the activity based on data received from the proximity device, and generate a notice.

In one example, the activity may include at least one of the user dispensing medication from the medication storage device and the user coming within a predetermined distance of the medication storage device. The medication storage system may include at least one sensor that communicates with the proximity device. The proximity device may be configured to be carried by the user. The medication storage system may include a controller configured to operate the dispense module. The controller may be located remotely from the medication storage device and the proximity device. The controller may be positioned in a common housing with the proximity device. The notice may be at least one of a text message and an audible message delivered to the user. The notice may be at least one of a summary report on usage of the medication storage device, or an alarm if the medication storage device is tampered with or moved. The notice may be generated if the pattern is broken.

Another embodiment of the present disclosure relates to a computer implemented method for monitoring medication use with a home automation system. The method includes receiving data regarding at least one of operation of a medication dispenser and proximity of a user to the medication dispenser, determining a pattern of the at least one of operation of the medication dispenser by the user and proximity of the user to the medication dispenser based on the received data, and generating a notice.

In one example, receiving data may include receiving data wirelessly from a device carried by the user. The method may include authenticating the user prior to permitting the user to operate the medication dispenser. Determining the pattern may include confirming that the at least one of operation of the medication dispenser by the user and proximity of the user to the medication dispenser occurs repeatedly in at least one of a given sequence and a given interval. The method may include delivering the notice to the device carried by the user. The method may include displaying the notice on a control panel of the home automation system. The method may include delivering the notice to a caregiver of the user. The method may include generating the notice if the pattern is broken. The notice may include a summary report on usage of the medication storage device. The notice may include an alarm if the medication storage device is tampered with or moved.

A further embodiment is directed to an apparatus for monitoring medication use with a home automation system. The apparatus includes a processor, a memory in electronic communication with the processor, and instructions stored in the memory. The instructions are executable by the processor to receive authentication data confirming identity of a user, receive data from a device carried by the user regarding operation of a medication dispenser by the user, determine a pattern of the user operating the medication dispenser based on the data, generate a notice, and deliver the notice to at least one of the user and a caregiver of the user.

In one example, the device may communicate with the medication dispenser. The device may include a proximity sensor. The instructions may be executable by the processor to receive data from the medication dispenser concerning operation of the medication dispenser. The instructions may be executable by the processor to continuously monitor operation of the medication dispenser by the user, and generate a notice if a sustained change in the pattern is detected. The notice may be generated if the pattern is broken. The notice may include a summary report on usage of the medication storage device. The notice may include an alarm if the medication storage device is tampered with or moved.

A further embodiment is directed to a computer implemented method for monitoring medical compliance using a home automation system. The method includes receiving instructions from a medical personnel concerning at least one medical-related activity, presenting the instructions to a patient via the home automation system, receiving feedback via the home automation system from at least one of the patient and a device used to collect medical-related information associated with the patient regarding compliance with the instructions, and delivering the feedback to the medical personnel.

In one example, the instructions may relate to consumption of medication, the device may be a medication dispensing device, and the feedback may include operation of the medication dispensing device to dispense medication for consumption by the patient. Presenting the instructions may include at least one of displaying a text message or generating an audio message at a control panel of the home automation system. Receiving feedback may include receiving an entry from the patient at a control panel of the home automation system. The entry may include at least one of confirmation of a medication consumption, a measurement from a medical device, and confirmation of a medical-related activity.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

Figure 1:
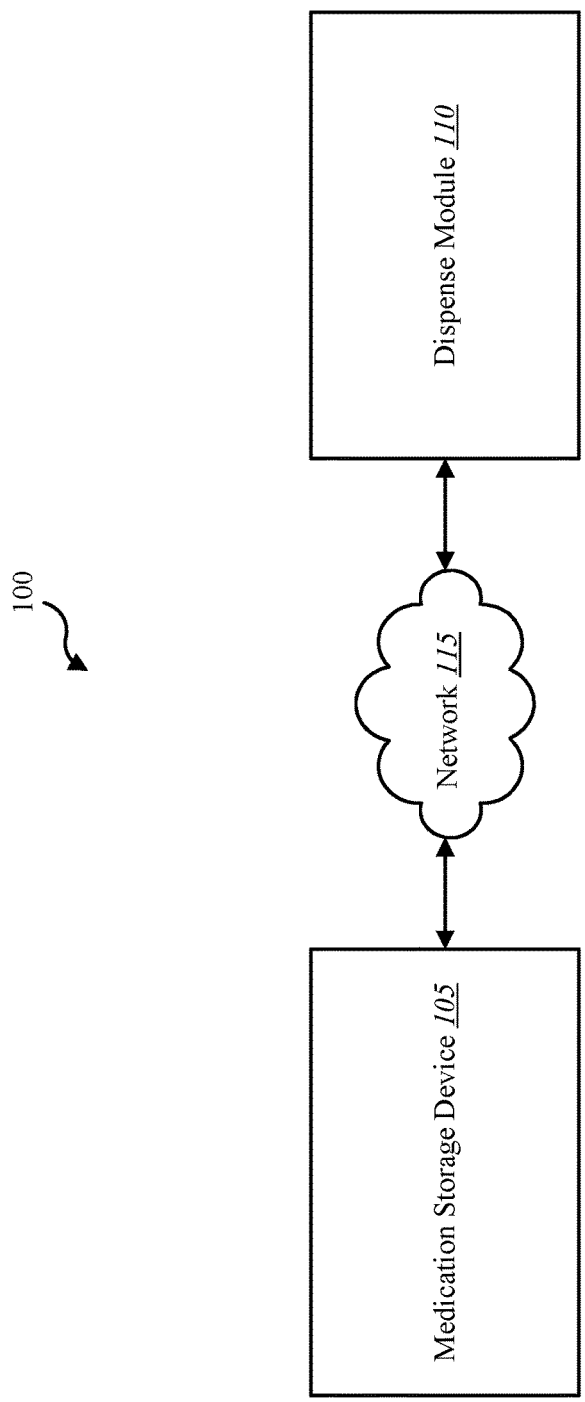
FIG. 1 is a block diagram of an environment in which the present systems and methods may be implemented.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The systems and methods described herein relate to home automation and home security, and related security systems and automation for use in commercial and business settings. As used herein, the phrase "home automation system" may refer to a system that includes automation features alone, security features alone, a combination of automation and security features, or a combination of automation, security and other features. While the phrase "home automation system" is used throughout to describe a system or components of a system or environment in which aspects of the present disclosure are described, such an automation system and its related features (whether automation and/or security features) may be generally applicable to other properties such as businesses and commercial properties as well as systems that are used in indoor and outdoor settings.

The following relates generally to medication storage, medication dispersement, medical compliance monitoring and feedback, and related systems and methods for carrying out the same, alone or in some combination. For most patients, taking the right amount of medication at specific times of the day and/or week is critical to maintaining good health. A number of pill dispensing products are available that organize a patient's pills by day of the week and even by times of the day. However, if the patient does not access the pill dispenser and actually consume the medication, the patient's health may be in jeopardy. Other medical-related tasks, regimes, and activities may be prescribed by a doctor and be expected to be carried out by a patient. Compliance with such doctor prescribed medications and/or activities may be difficult to confirm in many circumstances. While the present disclosure is focused primarily on medical-related subjects, the principles disclosed herein may have broader application related to communicating with a person and monitoring the person's activities in response to the communications.

One aspect of the present disclosure relates to a medication dispensing system that monitors a patient's use of a medication dispenser, which typically relates closely to the patient's intake of the dispensed medication. The medication dispensing system provides notices in the event the patient does not access the pill dispenser at predetermined times.

The present disclosure also relates to a medication dispensing system that automatically learns a patient's pattern of accessing a medication dispenser and then monitors for interruptions in that pattern as an indicator that the patient has missed taking, or at least dispensing, the medication. The present invention may provide reminders to a patient to take the routine medications when the user forgets to do so (or to notify a caregiver). The systems and method of the present disclosure may be well-suited for use by elderly persons who may more frequently forget to take his/her medications and may have difficulty remembering complex medication regimens. The systems and methods of the present invention may provide monitoring of the user's medication regime and automatically adapt to medication regime changes.

In one embodiment, the patient wears a device (e.g., a medical pendant), and another sensor is installed on a smart pill box (e.g., medication dispenser). When the sensor detects that the smart pill box is within a close proximity with the wearable device and/or that the pill box is operated/opened, the sensor sends a signal to a control center and the event is recorded. Over a small period of time (e.g., 1-2 days when medications are taken multiple times a day in a daily routine, or 1-2 weeks when medications are taken in some weekly routine), the patient's medication routine may be learned by the system. If the patient misses a routine medication intake, the system may send a reminder to the patient or to a caregiver of the patient (e.g., a relative or doctor/nurse) via, for example, a phone call, a text or audible message sent via a handheld computing device such as a smart phone or tablet computer, or via a control panel of a home automation and/or security system.

The control panel may be a control panel of a home automation system. The event may be recorded at the control panel or at a control center (e.g., central station or backend server) of the home automation system. The smart or learning capability of the systems and methods disclosed herein related to determining a pattern of medication intake/dispensing may be based at least in part on the frequency, time of day, day or week, and other criteria automatically collected by the system or manually entered by one or more persons (e.g., the patient or a caregiver).

Another aspect of the present disclosure relates to authenticating the identity of a user who access the medication dispenser. In at least some embodiments, the authenticating must be completed prior to permitting the user to access the medication dispenser. The authenticating may include, for example, confirmation that the user is carrying an identification device such as an identification pendant, bracelet, anklet, or the like. In another example, the authenticating may include entering a code on a user interface of the medication dispenser, voice recognition, fingerprint scan, face recognition, or the like. Other alternatives may be possible for completing an authenticating step in emergency situations. For example, a medication dispenser may be operable remotely by a caregiver or doctor in the event the patient is incapacitated (e.g., cannot perform typical authentication steps) but still requires intake of the medication held in the medication dispenser.

A further aspect of the present disclosure relates to a medical compliance monitoring system and related methods. In one embodiment, a home automation system is used to communicate between medical personnel and a patient. For example, a doctor may prescribe a medication regimen for a patient. The patient may receive notifications regarding details about the medication regimen via the home automation system (e.g., a control panel of the home automation system or a handheld mobile device in communication with the home automation system via a mobile application). The details may include at least one of a time when the medication should be taken, the name, size, color or other aspect of the medication itself, and an amount of medication to be consumed. The patient may provide feedback (e.g., via the control panel or handheld mobile device) about when and how much of the medication was consumed. In some examples, a pill dispenser, such as the smart pill dispenser described above, may automatically provide feedback related to operation of the pill dispenser to confirm, alone or in combination with the patient's direct feedback, consumption of the medication.

In another example, a medical personnel may communicate with the patient via the home automation system concerning other medical-related information that the patient collects using other devices or equipment. For example, the patient may receive a daily reminder via the home automation system to provide a blood pressure measurement, blood glucose measure, heart rate, body temperature, weight measurement, or the like. The patient may provide a response to the notice also via the home automation system. In some embodiments, the device used to collect the requested information may automatically communicate the information to the home automation system (e.g., via a wireless or wired connection to a control panel of the home automation system).

The medical personnel may communicate with the home automation system via a web-based portal or other easily accessible database. The medical personnel may access the portal and enter information specific to a particular patient. The information may include, for example, a physical therapy, medication, or measurement regimen, including instructions for sending the information to the patient. The portal may then communicate that information to the patient via the home automation system according a given schedule. The home automation system may communicate information from the patient, or instruments collecting information about the patient, to the portal. The portal may communicate notices and other information to the medical personnel (e.g., a notice that the patient has not taken a prescribed medication within a given timeframe).

FIG. 1 is a block diagram illustrating one embodiment of an environment 100 in which the present systems and methods may be implemented. In some embodiments, the systems and methods described herein may be performed at least in part on or using medication storage device 105 and a dispense module 110. Medication storage device 105 and dispense module 110 may communicate with each other via network 115. Although dispense module 110 is shown as a separate component from medication storage device 105, in other embodiments (e.g., the embodiment described below with reference to FIG. 2), dispense module 110 is integrated as a component of medication storage device 105, carried in a common housing with medication storage device 105, or at least operable without an intervening network 115.

Medication storage device 105 may store a plurality of medications and operate to dispense medications. The medications may be in the form of, for example, pills, capsules, syringes, and other single-dose or multi-dose containers. The medications may be in the form of, for example, solids, gels or liquids. Medication storage device 105 may include a plurality of cavities for storing the medication. Medication storage device 105 may include cavities that store medications for each of a plurality of times during the day, each day of the week, each day or week of the month, and the like. Medication storage device 105 may be referred to as a medication dispenser, a pill box, a pill dispenser, a medication delivery device, or the like. Medication storage device 105 may require input of a key, code, password, or other authentication or security indicators before permitting dispensing of the medication.

Dispense module 110 may monitor operation of medication storage device 105 to determine, for example, a pattern of dispensing the medication. The pattern may be based on, for example, a frequency of dispensing, an amount of medication dispensed, and the like during a time period such as an hour, day, week, or month. In some examples, as described below, dispense module 110 may infer access to and/or dispensing of medications at medication storage device 105 based on a proximity of the user relative to the medication storage device 105. Dispense module 110 may observe biological responses of one or more users to determine whether medication has been taken (e.g., blood pressure medicine taken to reduce blood pressure conditions in the user) as an indicator that the medication has been dispensed from medication storage device 105.

Medication storage device 105 may include, for example, security measures to prohibit unauthorized access of medications held therein. For example, medication storage device 105 may require entry of a code, keyword, fingerprint, voice recognition, retinal scan, or the like to confirm that the person accessing medication storage device 105 is authorized to do so. In only some examples, medication storage device 105 requires a plurality of authentication or security inputs prior to permitting dispensing of the medication.

Dispense module 110 may operate to control at least some functions of medication storage device 105. For example, dispense module 110 may operate the authentication features of medication storage device 105. In other examples, dispense module 110 may control messaging to a user or caregiver of a user in response to interaction with the user with medication storage device 105. For example, if dispense module 110 determines that a user has not accessed medication held in medication storage device 105 according to a predetermined schedule or regimen, dispense module 110 may generate and deliver a message to the user or caregiver of the user as a reminder to access the medication via medication storage device 105. In another example, dispense module 110 determines that the medication storage device 105 has been accessed at an inappropriate time, such as more frequently than should occur according to a predetermined schedule or regimen.

Dispense module 110 may communicate with a user via, for example, a display, a speaker system that provides an audible message, an appliance located on the property (e.g., home) being monitored by the home automation system, or the like. Medication storage device 105 may communicate with a remote device such as, for example, a handheld mobile device carried by the patient, a caregiver of the patient, a backend server, or the like.

Dispense module 110 may automatically determine a pattern of dispensing medication to a user via medication storage device 105. The pattern may be determined based on, for example, a frequency of operating the medication storage device 105 to dispense the medication over a period of hours, days, weeks, or the like. In one example, dispense module 110 determines a pattern of taking medication when the medication storage device 105 has been accessed every other day between the hours of 5:00 and 6:00 p.m. for three successive periods. In another example, dispense module 110 determines a pattern of taking medication three times per day when medication storage device 105 is accessed between the hours of 7:00 a.m. and 9:00 a.m., between the hours of 12:00 p.m. and 1:00 p.m., and between the hours of 6:00 p.m. and 8:00 p.m. each day for at least two days.

A greater level of certainty that a specific pattern has been established may be confirmed the more times dispense module 110 observes operation of medication storage device 105 according to the initially-determined pattern. For example, a level of certainty that a pattern has been established for taking a medication every other day between the hours of 5:00 and 6:00 p.m. may increase after 10 days of such a routine as opposed to only 2, 3 or 5 days of such a routine.

In some embodiments, dispense module 110 may be operated into an active or learn state, either automatically or manually, until such time as a pattern has been established with a desired level of certainty. In one embodiment, a user manually turns off the active or learn state upon attaining the desired level of certainty. After the pattern is established, dispense module 110 may continue to operate with a high level of certainty of a particular pattern. In other examples, a user may manually enter a schedule or pattern such as a drug regimen directly into dispense module 110 as opposed to an automated determination of the pattern based on behavior of one or more users accessing medication storage device 105 over time.

Once the dispense module 110 determines at least a proposed or initial pattern is established, dispense module 110 may continue to increase the certainty of that pattern by, for example, further monitoring operation of medication storage device 105, receiving feedback from a user or caregiver of the user in response to inquiries from dispense module, or receiving feedback from the user that the initial pattern is not accurate.

Dispense module 110 may generate a notice related to, for example, usage of medication storage device 105. In one example, the notice is generated if the determined pattern of usage is broken. The notice may include a report such as a summary report regarding usage of the medication storage device. The notice may include an alarm if, for example, the medication storage device 105 is tampered with or moved. The notice may include a message that is delivered to one or more parties, such as a caregiver or the person operating medication storage device 105.

As mentioned above, dispense module 110 may operate using medication storage device 105 or another device such as, for example, a pendant, bracelet, anklet, or the like carried by the user. Dispense module 110 may be arranged in communication with, in addition to medication storage device 105, a back end server, a central station of a home automation system, or a mobile device carried by the user or other person (e.g., a smartphone, tablet computer, laptop computer, or the like).

Network 115 may utilize any available communication technology such as, for example, Bluetooth, ZigBee, Z-wave, infrared (IR), radio frequency (RF), and near field communication (NFC). In other examples, network 115 may include cloud networks, local area networks (LAN), wide area networks (WAN), virtual private networks (VPN), wireless network (using 802.11, for example), and/or cellular networks (e.g., using 3G and/or LTE), etc. In some embodiments, network 115 may include the Internet.

Figure 2:
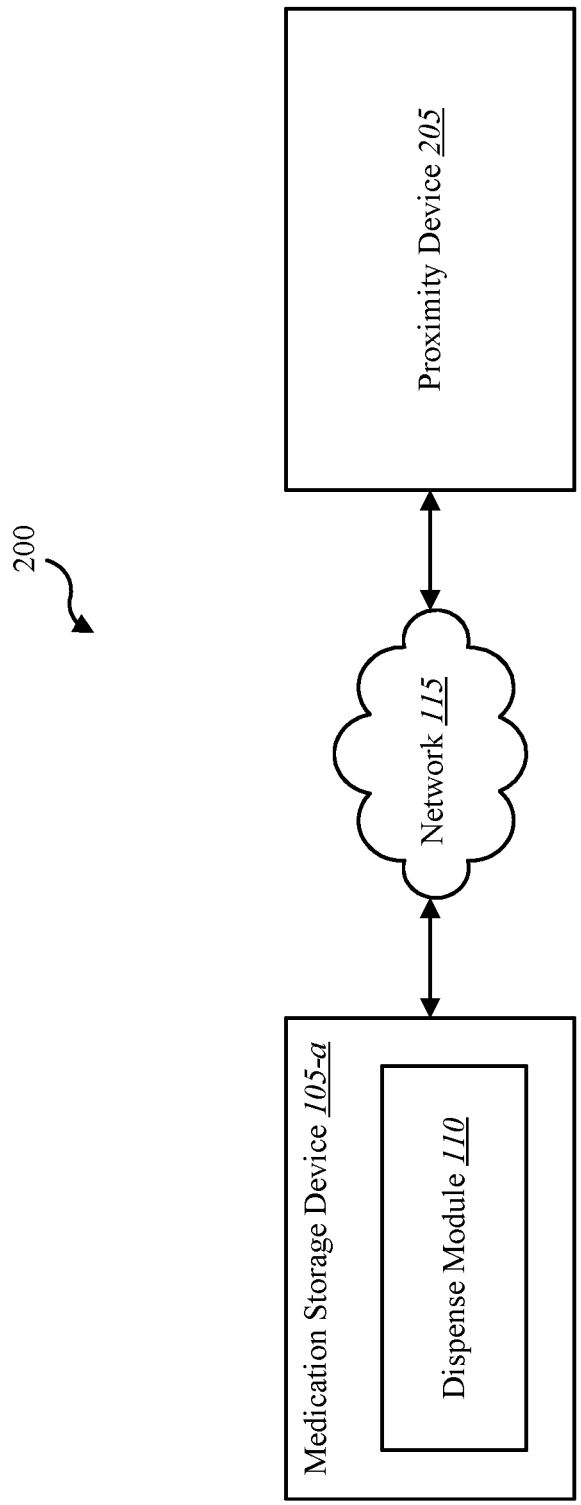
FIG. 2 is a block diagram of another environment in which the present systems and methods may be implemented.

FIG. 2 is a block diagram illustrating one embodiment of an environment 200 in which the present systems and methods may be implemented. Environment 200 may include at least some of the components of environment 100 described above. Environment 200 may include, in addition to medication storage device 105-a, dispense module 110, and network 115, a proximity device 205. Dispense module 110 is shown as part of medication storage device 105-*a*. Dispense module 110 may be a component of and may be integrally formed as part of medication storage device 105-*a* (e.g., housed within a common housing, operable using a common power source, and the like).

Proximity device 205 operates to determine when a person carrying proximity device 205 is within a zone or predetermined area adjacent to medication storage device 105-*a*. The operation of medication storage device 105-*a* to dispense a medication may be inferred from a user being positioned in close proximity to medication storage device 105-*a*, as determined by proximity device 205. The distance or zone between the proximity device 205 and medication storage device 105-*a* to make such an inference may be in the range of, for example, about 1 inch to about 3 feet. In one embodiment, proximity device 205 operates based physical contact between the user and medication storage device 105-*a*, or physical contact between proximity device 205 and one or more features of medication storage device 105-*a*.

In some examples, proximity device 205 is embodied in a wearable device carried by a user (e.g., a user who is preauthorized to access the medication). In one example, proximity device 205 is housed in a pendant carried by a user, an anklet or bracelet worn by the user, or a fab carried by the user. In some embodiments, the system infers that whoever is carrying proximity device 205 is authorized to access medication held in medication storage device 105-*a*. In other examples, a separate authentication step is required to confirm identify of the person carrying proximity device 205. It may be possible to circumvent the authentication step for operating medication storage device 105-*a* based on, for example, an emergency situation which meets a predetermined set of criteria (e.g., incapacity of the person intended to take the medication). Proximity device 205 may communicate with dispense module 110 via, for example, network 115.

Figure 3:
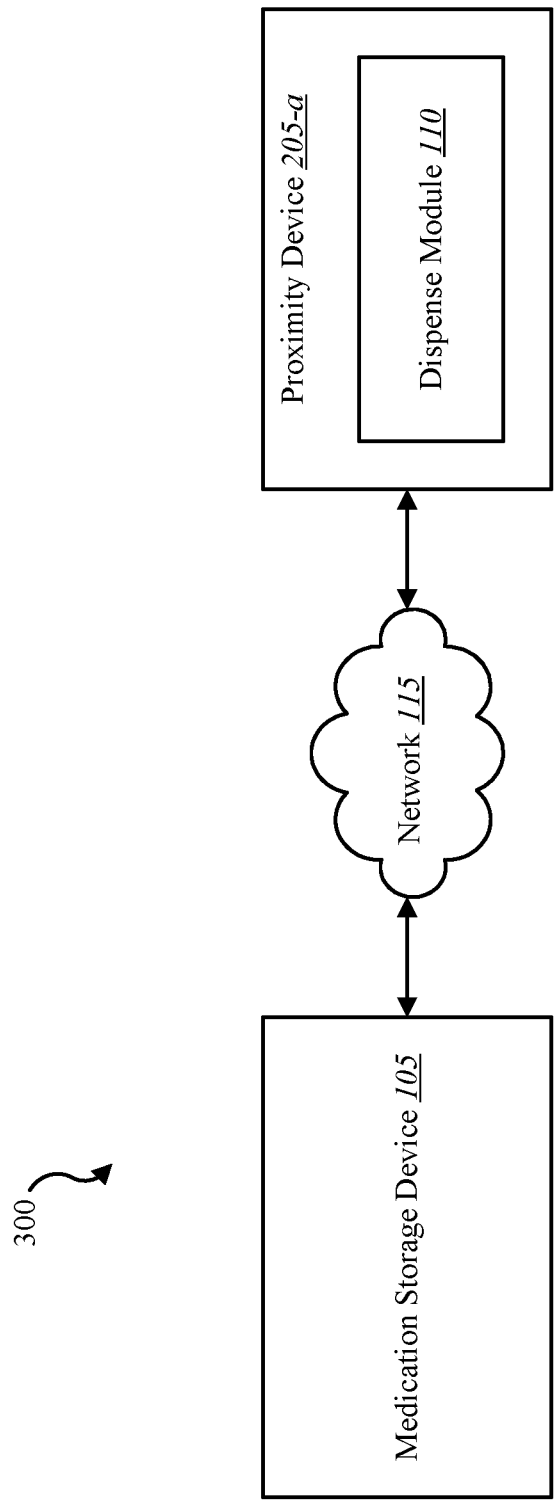
FIG. 3 is a block diagram of another environment in which the present systems and methods may be implemented.

FIG. 3 is a block diagram illustrating one embodiment of an environment 300 in which the present systems and methods may be implemented. Environment 300 may include at least some of the components of the environments 100, 200 described above. Environment 300 may include, in addition to medication storage device 105, proximity device 205-*a*, which includes dispense module 100. Proximity device 205-*a* may operate, at least in part, some aspects of dispense module 110 described above. Dispense module 110 may be housed in a common housing with proximity device 205-*a* and carried by, for example, a user or other person authorized to access medications from medication storage device 105.

In some embodiments, some functionality of dispense module 110 may be carried out using the same device that includes proximity device 205-*a*, while other functionality of dispense module 110 may be carried out by other devices, systems, or methods, such as using medication storage device 105, a back end server, a central station, handheld computing device, or the like. Medication storage device 105, proximity device 205, and dispense module 110 may communicate with each other using a variety of communication mediums, which may be part of network 115.

Figure 4:
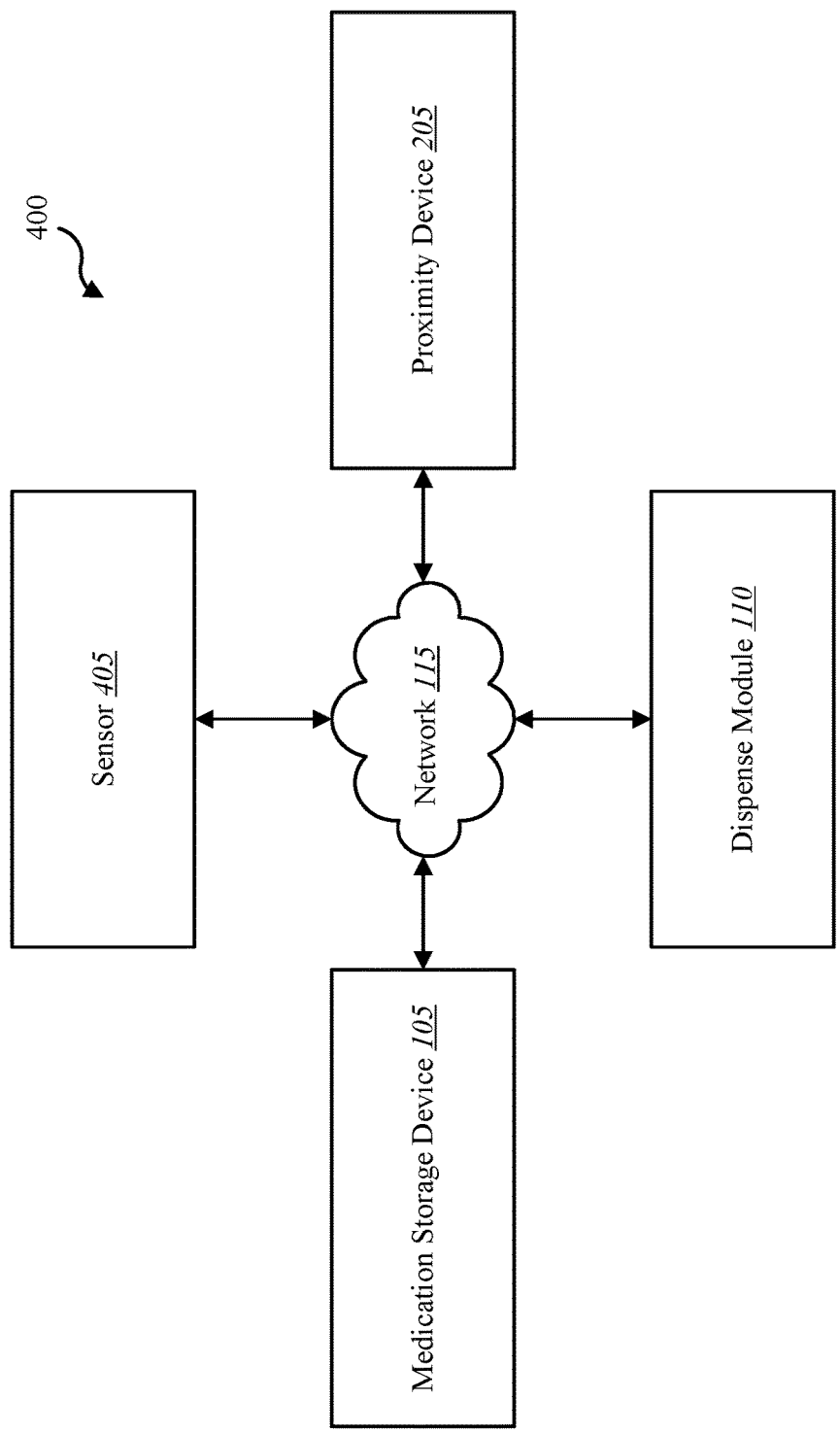
FIG. 4 is a block diagram of another environment in which the present systems and methods may be implemented.

FIG. 4 is a block diagram illustrating one embodiment of an environment 400 in which the present systems and methods may be implemented. Environment 400 may include at least some of the components of environments 100, 200, 300 described above. Environment 400 may include medication storage device 105, dispense module 110, proximity device 205, and a sensor 405.

Sensor 405 may operate to determine, for example, operation of medication storage device 105, dispensing of medication to a user, proximity of the user relative to medication storage device 105, biometrics of the user, and the like. Sensor 405 may be integrated into medication storage device 105 and/or proximity device 205 as a component thereof. Additionally, or alternatively, sensor 405 may be a sensor that provides data for operation of a home automation system. Sensor 405 may include, for example, a camera sensor, an audio sensor, a forced-entry sensor, a shock sensor, a proximity sensor, a boundary sensor, an appliance sensor, a light fixture sensor, a temperature sensor, a light beam sensor, a three-dimensional (3D) sensor, a motion sensor, a smoke sensor, a glass-break sensor, a door sensor, a video sensor, a carbon monoxide sensor, an accelerometer, a global positioning system (GPS) sensor, a Wi-Fi positioning sensor, a capacitance sensor, a radio frequency sensor, a near-field sensor, a heartbeat sensor, a breathing sensor, an oxygen sensor, a carbon dioxide sensor, a brainwave sensor, a voice sensor, a touch sensor, and the like. Although sensor 405 is depicted as a separate component from medication storage device 105, proximity device 205, network 115, and dispense module 110, sensor 405 may be connected directly to or housed with any one of those components or other components of environment 400. Additionally, or alternatively, sensor 405 may be integrated into a home appliance or fixture. In some examples, sensor 405 may operate to assist in authenticating a user who attempts to operate medication storage device 105, proximity device 205, or other feature or component of a home automation system relating to dispensing of a medication.

Sensor 405 may include a plurality of sensors having various sensor capability. For example, sensor 405 may sense physiological responses of one or more persons such as, for example, a heart rate, a sleeping state, a body temperature, or the like. Sensor 405 may include geo tracking capabilities such as identifying a geographic location or a direction of travel, or an orientation of a person's body (e.g., standing up or lying down). Sensor 405 may be associated with a building such as a home, and data from sensor 405 may indicate a location and/or activity of one or more persons in the home. In some examples, sensor 405 may operate, at least in part, to determine whether a person has performed an action (e.g., accessed medication storage device 105) when other features such as proximity device 205 indicate that the person is within a predetermined zone or distance relative to the medication storage device 105.

Feedback from sensor 405 may be used to create and/or select among various messages that may be sent to the user or a caregiver of the user. For example, if proximity device 205 indicates that a person is within a predetermined range which may infer operation of medication storage device 105, and sensor 405 indicates that no medication was actually dispensed from medication storage device 105, a message may be sent to a caregiver of the user that the medications were not dispensed and/or taken. In another example, sensor 405 may a physiological condition such as monitor blood pressure of the user who is intended to take the medication, and sensor 405 indicates that a blood pressure did not change within a predetermined time period after the user accessed medication storage device 105 (e.g., as determined by operation of proximity device 205 and/or other features indicating and/or inferring that the medication has been dispensed). A message may then be sent to the user or caregiver of the user that the medication is either ineffective and/or has not been taken.

Figure 5:
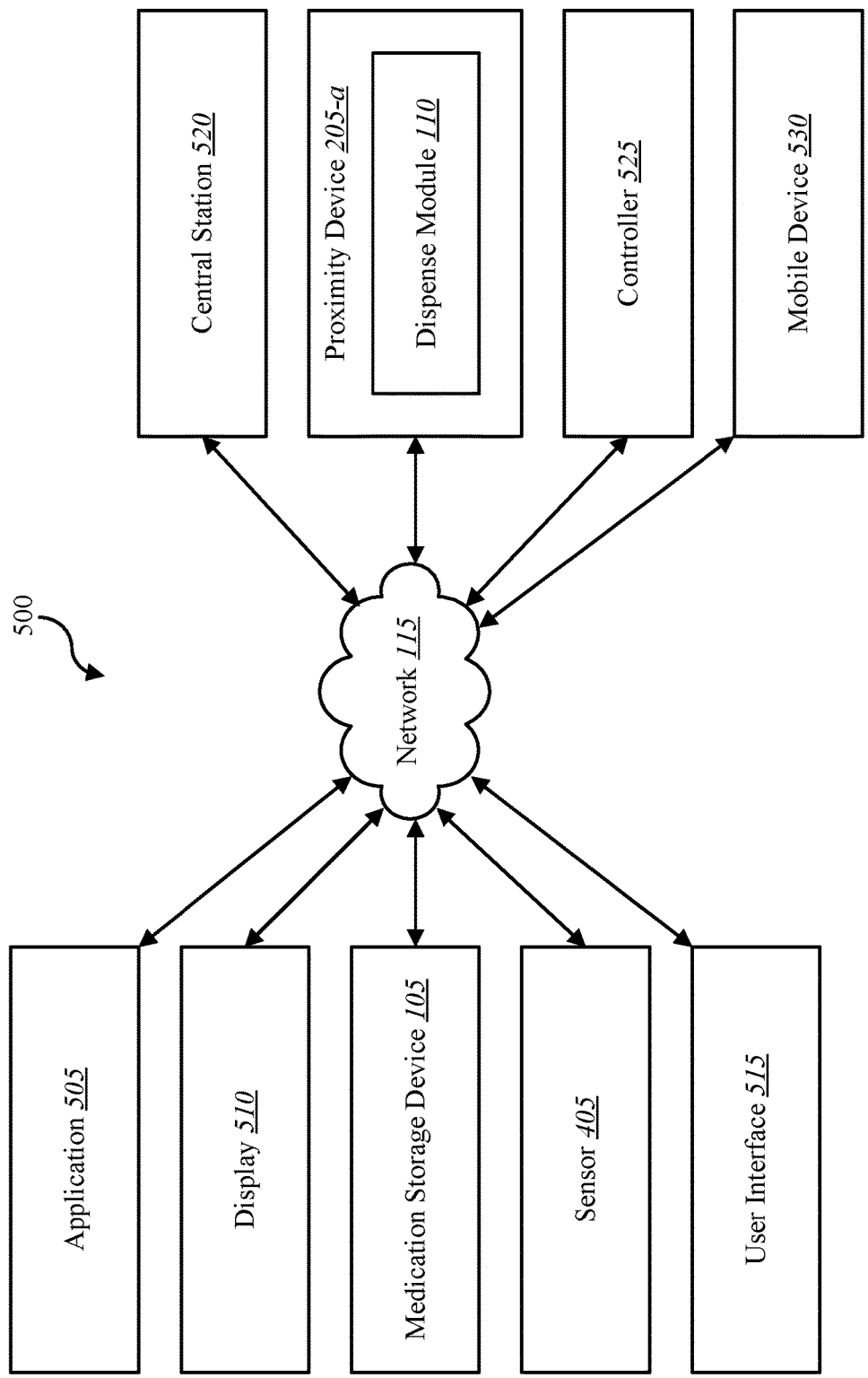
FIG. 5 is a block diagram of another environment in which the present systems and methods may be implemented.

FIG. 5 is a block diagram illustrating one embodiment of an environment 500 in which the present systems and methods may be implemented. Environment 500 may include at least some of the same components as environments 100, 200, 300, 400 described above. Environment 500 may include, in addition to medication storage device 105, proximity device 205-a, dispense module 110, and sensor 405, an application 505, a display 510, a user interface 515, a central station 520, a controller 525, and a mobile device 530. Any of the components of environment 500 may be included in the environments 100, 200, 300, 400 described above.

The systems, devices, and methods described above with reference to FIGS. 1-4 may be part of a home automation system. It is typical for home automation systems to include, in addition to sensor 405, other features of environment 500 shown in FIG. 5. For example, application 505 may allow a user (e.g., a user who operates medication storage device 105) to control an aspect of the monitored property including security, energy management, locking and unlocking doors, checking the status of the door, locating a user or item, controlling lighting, thermostat, or cameras, and receiving notifications regarding a current condition or anomaly associated with a home, office, place of business, and the like (e.g., a property). In some configurations, application 505 may enable medication storage device 105 to communicate with other components of environment 500 such as, for example, proximity device 205-a, sensor 405, central station 520, controller 525, and/or mobile device 530. In one example, application 505 may provide the user interface 515 to display an automation, security and/or energy management content on a device such as a control panel of the home automation system. Thus, application 505, via user interface 515, may allow users to control aspects of their home, office, and/or other type of property. Further, application 505 may be installed on medication storage device 105 or other device of the home automation system such as, for example, a control panel thereof.

Application 505 may facilitate generation of an alarm/notification in response to the operation of medication storage device 105 or failure of a user to operate and/or access medications carried by medication storage device 105 according to a predetermined pattern. Application 505 may coordinate with and/or operate concurrently with dispense module 110, sensor 405, and other features of environment 500 concerning operation of medication storage device 105, dispensing of medication and/or actual administration of the medication to one or more persons.

Display 510 may include, for example, a digital display as part of, for example, a control panel of environment 500 (e.g., a control panel of a home automation system). Display 510 may be part of medication storage device 105 and/or proximity device 205-a. Display 510 may be provided via devices such as, for example, a desktop computer or mobile device 530. In at least some examples, display 510 may be either permanently mounted (e.g., mounted to a wall of the home), or may be a mobile device or accessible via mobile device 530. User interface 515 may be integrated into display 510. Such user interface 515 may include a plurality of menus, screens, microphones, speakers, cameras, and other capability that permit interaction between the user and the home automation system, or components of environment 500. Additionally, or alternatively, user interface 515, with display 510, may be integrated into medication storage device 105 and/or proximity device 205-a.

Display 510 and user interface 515 may provide input of data that is used by dispense module 110 for purposes of, for example, establishing a pattern of dispensing medication and/or accessing medication storage device 105.

Central station 520 may provide back end support for the home automation system. Central station 520 may provide storage of data such as, for example, use data related to medication storage device 105 and/or dispense module 110. Central station 520 may also provide back end support such as customer service and/or may facilitate communications with a caregiver or others if the determined pattern of dispensing medication via medication storage device 105 is not being followed.

Controller 525 is shown as a separate component from medication storage device 105 and proximity device 205-a. In other examples, controller 525 provides logic and/or processing functionality that supports, for example, operation of dispense module 110.

Mobile device 530 may provide a way for controlling and/or communicating with medication storage device 105, proximity device 205-a, and/or dispense module 110. In one example, mobile device 530 is carried by a caregiver of a user who is intended to operate medication storage device 105 to dispense medication. Dispense module 110 may send a message, alarm, or the like to the caregiver via mobile device 530. The caregiver may send a responsive message that is delivered to the user. In some examples, mobile device 530 may provide a remotely-positioned person (e.g., a caregiver, doctor, or the like) to operate medication storage device 105 remotely.

Figure 6:
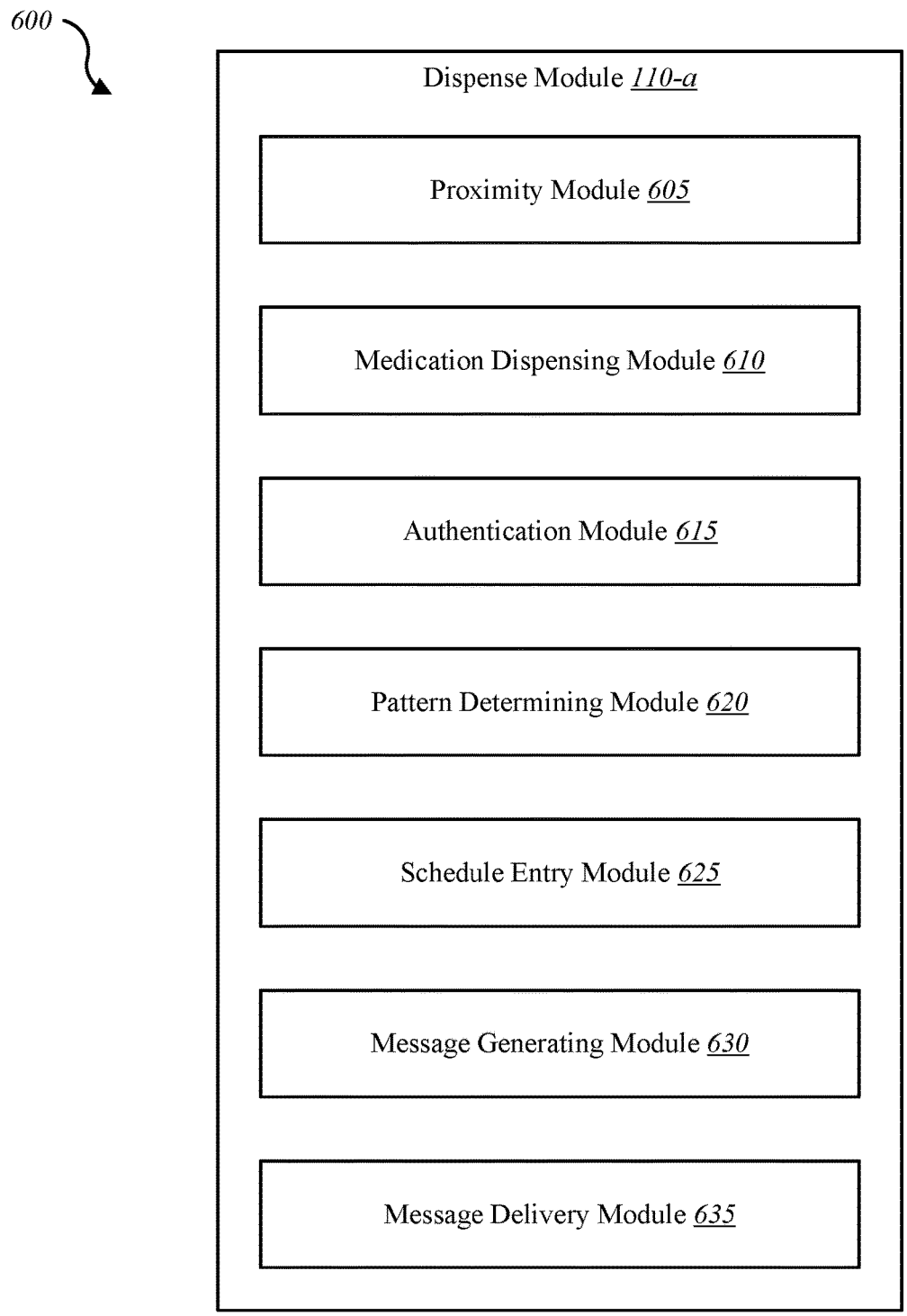
FIG. 6 is a block diagram of a dispense module of the environments shown in FIGS. 1-5.

FIG. 6 is a block diagram illustrating an example dispense module 110-a. Dispense module 110-a may be one example of the dispense module 110 described above with reference to FIGS. 1-5. Dispense module 110-a may include a proximity module 605, a medication dispensing module 610, an authentication module 615, a pattern determining module 620, a schedule entry module 625, a message generating module 630, and a message delivery module 635. In other examples, dispense module 110-a may include more or fewer of the modules shown in FIG. 6.

Proximity module 605 may receive data from, for example, proximity device 205 concerning the location of a user relative to the medication storage device 105. Proximity module 605 may determine whether the person carrying proximity device 205 is within a predetermined range, and thereby determine whether the user probably operated the medication storage device 105. Proximity module 605 may determine the proximity of the user to other features or devices such as, for example, an appliance such as a refrigerator, a vehicle, a swimming pool or bathtub, or other device or related activity which may be pertinent to activities a user is permitted to engage in after having taken a given medication.

Medication dispensing module 610 may operate to determine when medication storage device 105 has been operated to dispense medication. Medication dispensing module 610 may determine what type of medication has been dispensed, the frequency of dispensing, the amount of medication dispensed. The dispensing information may be entered manually by one or more users, or may be determined automatically based on operation of one or more devices (e.g., medication storage device 105).

Authentication module 615 may operate to determine an identity of a person accessing medication storage device 105. For example, authentication module 615 may determine based on, for example, input of a fingerprint, voice sample, retinal scan, pin code, or other identification information whether the person accessing the medication dispensing module is authorized to do so. Authentication module 615 may operate based on a device being carried by the person accessing the medication storage device 105. For example, a person carrying proximity device 205 may meet the authentication requirements determined using authentication module 615. The data from authentication module 615 may be used to control operation of medication storage device 105. For example, if authentication module 615 determines that the person identified is not authorized to dispense medication, no dispensing may be permitted. Authentication module 615 may generate a notice, alarm, inquiry or the like to determine with greater accuracy the identification of the person and/or the reason why access is being attempted.

Pattern determining module 620 may receive data related to operation of the medication storage device 105, and based on that data determine a pattern of medication dispensing. The pattern may be confirmed based on the amount and/or type of use data received. For example, a preliminary or initial proposed pattern may be established based on 2 to 5 data inputs, and a finalized or confirmed pattern may be established after 10 to 20 data points.

New patterns may be determined and confirmed automatically based on ongoing use and operation of medication storage device 105. Pattern determining module 620 may pose inquiries to and receive feedback from the user to accelerate identification and modification of a given pattern. When a potential change in the pattern occurs based on a change in, for example, frequency of operating the medication storage device 105, pattern determining module 620 may move into a learn mode. The learn mode may be terminated after a certain number of data points are received or upon entry of a confirmation from the user. Pattern determining module 620 may determine a pattern based on a combination of user input and automated monitoring and/or feedback related to use of the medication storage device 105 and/or proximity device 205.

Schedule entry module 625 may provide for manual entry by a user of a medication regimen/schedule. Schedule entry module 625 may confirm that the actual dispensing of medication (e.g., as determined by operation of medication storage device 105 and/or proximity device 205) matches the entered schedule. Schedule entry module 625 may generate notices, alarms, or the like in the event the manually entered schedule is not properly followed.

Message generating module 630 may operate to generate messages, alarms, inquiries, and the like in response to deviations from a determined pattern of dispensing medication. The messages generated may be delivered via message delivery module 635. Messages may be delivered via, for example, a display (e.g., display 510), a user interface (e.g., user interface 515), a mobile device (e.g., mobile device 530), or the like delivered via, for example, medication storage device 105, proximity device 205, or the like. Information received in response to any messages sent by message delivery module 635 may be utilized by any one of the proximity module 605, medication dispensing module 610, authentication module 615, pattern determining module 620, and/or schedule entry module 625 to determine whether the alarm condition has been resolved or whether further inquiries, data or the like are needed.

Figure 7:
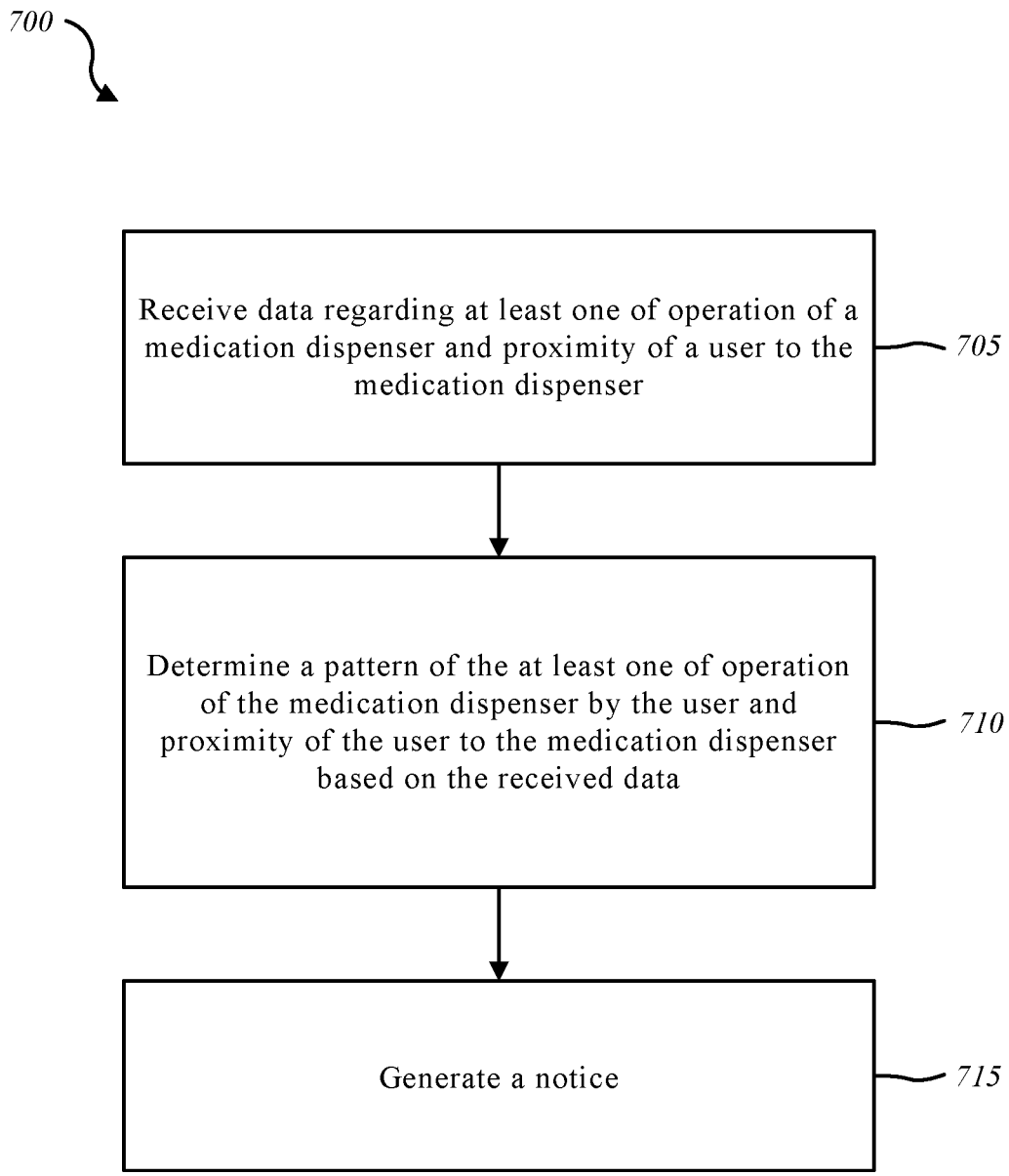
FIG. 7 is a flow diagram illustrating a method for communicating messages using a home automation system.

FIG. 7 is a flow diagram illustrating one embodiment of a method 700 for monitoring medication use with a home automation system. In some configurations, the method 700 may be implemented by the dispense module 110 shown and described with reference to FIGS. 1-6. In other examples, the method 700 may be performed generally by medication storage device 105 and proximity device 205 shown in FIGS. 1-5, or even more generally by environments 100, 200, 300, 400, 500 shown in FIGS. 1-5.

At block 705, the method 700 includes receiving data regarding at least one of operation of a medication dispenser and proximity of the user to the medication dispenser. Block 710 includes determining a pattern of the at least one of operation of the medication dispenser by the user and proximity of the user to the medication dispenser based on the received data. At block 715, the method 700 includes generating a notice.

Method 700 may also include receiving data wirelessly from a device carried by the user. The method 700 may include authenticating the user prior to permitting the user to operate the medication dispenser. Determining the pattern may include confirming that the at least one of operation of the medication dispenser by the user and proximity of the user to the medication dispenser occurs repeatedly in at least one of a given sequence and a given interval. Method 700 may include delivering the notice to the device carried by the user. The method 700 may include displaying the notice on a control panel of the home automation system. The method 700 may include generating the notice when the pattern is broken, including a summary report on usage of the medication storage device as part of the notice, or including an alarm as part of the notice if, for example, the medication storage device is tampered with or moved.

Figure 8:
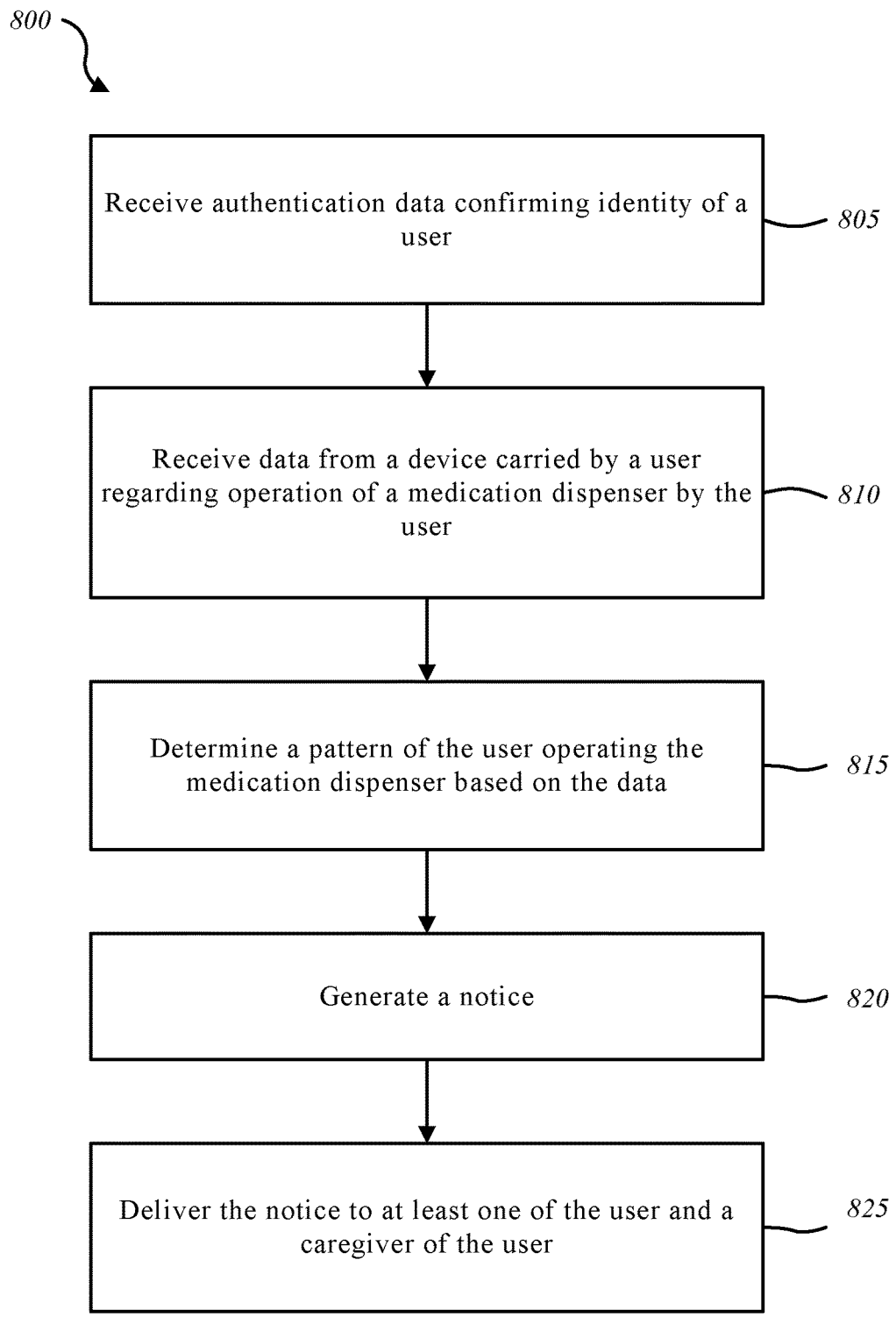
FIG. 8 is a flow diagram illustrating another method for communicating messages using a home automation system.

FIG. 8 is a flow diagram illustrating one embodiment of a method 800 for monitoring medication use with a home automation system. In some configurations, the method 800 may be implemented by the dispense module 110 shown and described with reference to FIGS. 1-6. In other examples, the method 800 may be performed generally by medication storage device 105 or proximity device 205 shown in FIGS. 1-5, or even more generally by environments 100, 200, 300, 400, 500 shown in FIGS. 1-5.

At block 805, the method 800 includes receiving authentication data confirming identity of a user. Block 810 includes receiving data from a device carried by the user regarding operation of the medication dispenser by the user, block 815 includes determining a pattern of the user operating the medication dispenser based on the data. Block 820 includes generating a notice, and block 825 includes delivering the notice to at least one of the user and a caregiver of the user.

According to method 800, the device may communicate with the medication dispenser. The device may include a proximity sensor. The method 800 may include receiving data from the medication dispenser concerning operation of the medication dispenser. The method 800 may include continuously monitoring operation of the medication dispenser by the user and generating a notice if, for example, a sustained change in the pattern is detected.

Figure 9:
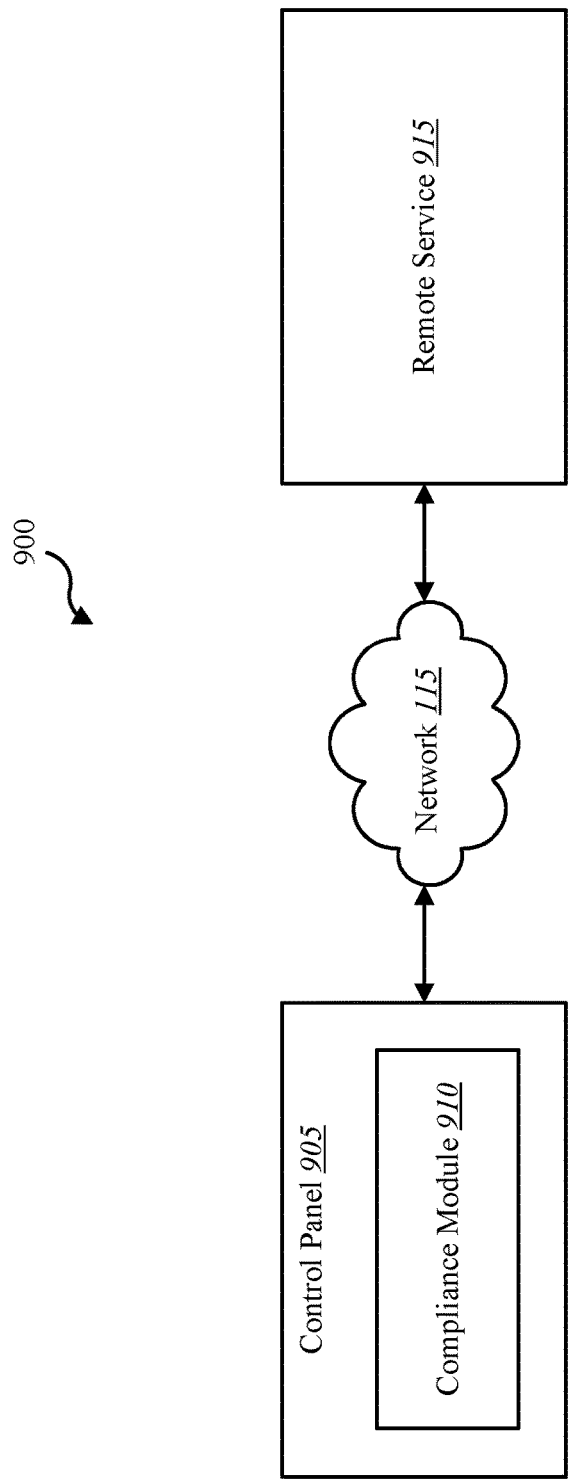
FIG. 9 is a block diagram of another environment in which the present systems and methods may be implemented.

As mentioned above, another aspect of the present disclosure relates to systems and methods for medical compliance monitoring, which is described in further detail with reference to FIGS. 9-12. FIG. 9 is a block diagram illustrating one embodiment of an environment 900 in which the present systems and methods may be implemented. In some embodiments, the systems and methods described herein may be performed, at least in part, on or using a control panel 905 of a home automation system. Environment 900 may include a compliance module 910. The compliance module 910 may be operated by control panel 905. Environment 900 may further include a remote service 915. Remote service 915 may communicate with control panel 905 via network 115. In other embodiments, compliance module 910 is operable independent of control panel 905 and remote service 915. Additionally, or alternatively, compliance module 910 may be operated at least in part by remote service 915, and/or by both control panel 905 and remote service 915.

Control panel 905 may be one example of a control device used as part of a home automation system for controlling certain aspects of the home automation system. In one example, control panel 905 includes a display, a user interface, a speaker, and/or a microphone to provide interaction with one or more users of a property where the control panel is located. Control panel 905 may include a controller, memory, a transceiver, and other capabilities for processing data, storing data, and communicating data to/from other devices and/or systems such as, for example, remote service 915. In some arrangements, a single control panel 905 controls a home automation system for a single property. Control panel 905 may include a plurality of slave control panels that are positioned throughout the property. Control panel 905 may be considered a computing device capable of operating, for example, compliance module 915 or aspects thereof.

Remote service 915 may provide a medium or service for communicating between medical personnel and one or more persons (e.g., patients). In one example, remote service 915 is structured as a web-based portal or other system that is accessible by a plurality of persons from many different locations. Remote service 915 may provide the ability for medical personnel to communicate with a plurality of different patients, via, for example, a plurality of differing control panels 905. Remote service 915 may also facilitate communication between a plurality of different medical personnel and a single patient via, for example, control panel 905.

In one embodiment, remote service 915 facilitates sending instructions to a patient from one or more medical personnel particularly in the context of medical compliance monitoring. Other applications may be possible outside of the medical field including, for example, sports/fitness, finances, family or personal counseling/therapy, academics, and the like. Remote service 915 may provide a medium for any of those applications to provide instructions and/or notices to one or more persons via a home automation system (e.g., via control panel 905). Compliance module 910 may operate to present the instructions to the patient (or other person), receive feedback concerning compliance with the instructions, and deliver the feedback to the remote service 915 for review by the medical personnel (or other person sending and/or generating the instructions).

The subject of the instructions may vary widely depending on the application. In a medical compliance application, the instructions may relate to, for example, a medication regimen, a physical therapy regimen, a status of a physiological condition, a nutritional status and/or intake, or other therapies whether mental, emotional, or physical. Compliance module 910 may cooperate with control panel 905 to present the instructions to a patient, a caregiver of a patient, an adult (e.g., when the patient is a minor), or other responsible party. The instructions may be presented on the control panel 905 as, for example, a text display, lighting sequence, audio message, video message, alarm, or the like. Additionally, or alternatively, control panel 905 may deliver the instructions or related message via other devices that are in communication with control panel 905 such as, for example, a hand-held mobile device, a slave control panel, a speaker system located on the property monitored by the home automation system, an appliance such as a TV or other display, or the like.

In some examples, compliance module 910 may receive confirmation from one or more persons that the instructions or other messages have been received and/or understood. Compliance module 910 may operate to receive feedback from one or more persons or devices in response to the conveyed instructions. The feedback may be received in many forms including, for example, a manual input to control panel 905, a voice command, a text message received at control panel 905, or other information conveyed from a separate device such as, for example, a blood pressure monitor, a thermometer, a glucose monitor, a weight scale, or an implanted medical device, any of which may communicate with control panel 905 or some other feature of the home automation system. In one example, as will be described below, compliance module 910 may receive feedback from a medication dispensing device indicating that medication has been dispensed and/or that a certain person has accessed the medication dispensing device. The feedback from such devices may be sent automatically upon measuring or monitoring certain behavior, physical properties, or attributes of one or more persons in response to the received instructions. Additionally, or alternatively, the device may be manually linked or coupled to the home automation system (e.g., control panel 905) in order to provide the feedback in response to the received instructions. In one example, a blood pressure monitoring device may be connected directly to control panel 905 with a cable or with a wireless connection (e.g., via network 115).

Compliance module 910 may also monitor the amount of time between when the instructions are provided to the patient or other person and when feedback is received related to the instructions. Predetermined threshold time periods may be set within which feedback should be received or else an alarm or notice is generated by compliance module 910 indicating non-compliance with the instructions. The notice of non-compliance may be delivered to remote service 915 and thereafter to one or more medical personnel. Additionally, or alternatively, the non-compliance notice may be delivered to other parties such as, for example, a caregiver, a neighbor, the patient, or emergency personnel. The non-compliance notice may be delivered to a remote hand-held computing device that operates a mobile application that communicates with compliance module 910 or other feature of the home automation system. Additionally, or alternatively, the non-compliance notice may be delivered via another medium such as, for example, email, voice message, text message, or the like. The non-compliance notice may be delivered directly to medical personnel via a communication system that bypasses remote service 915.

Figure 10:
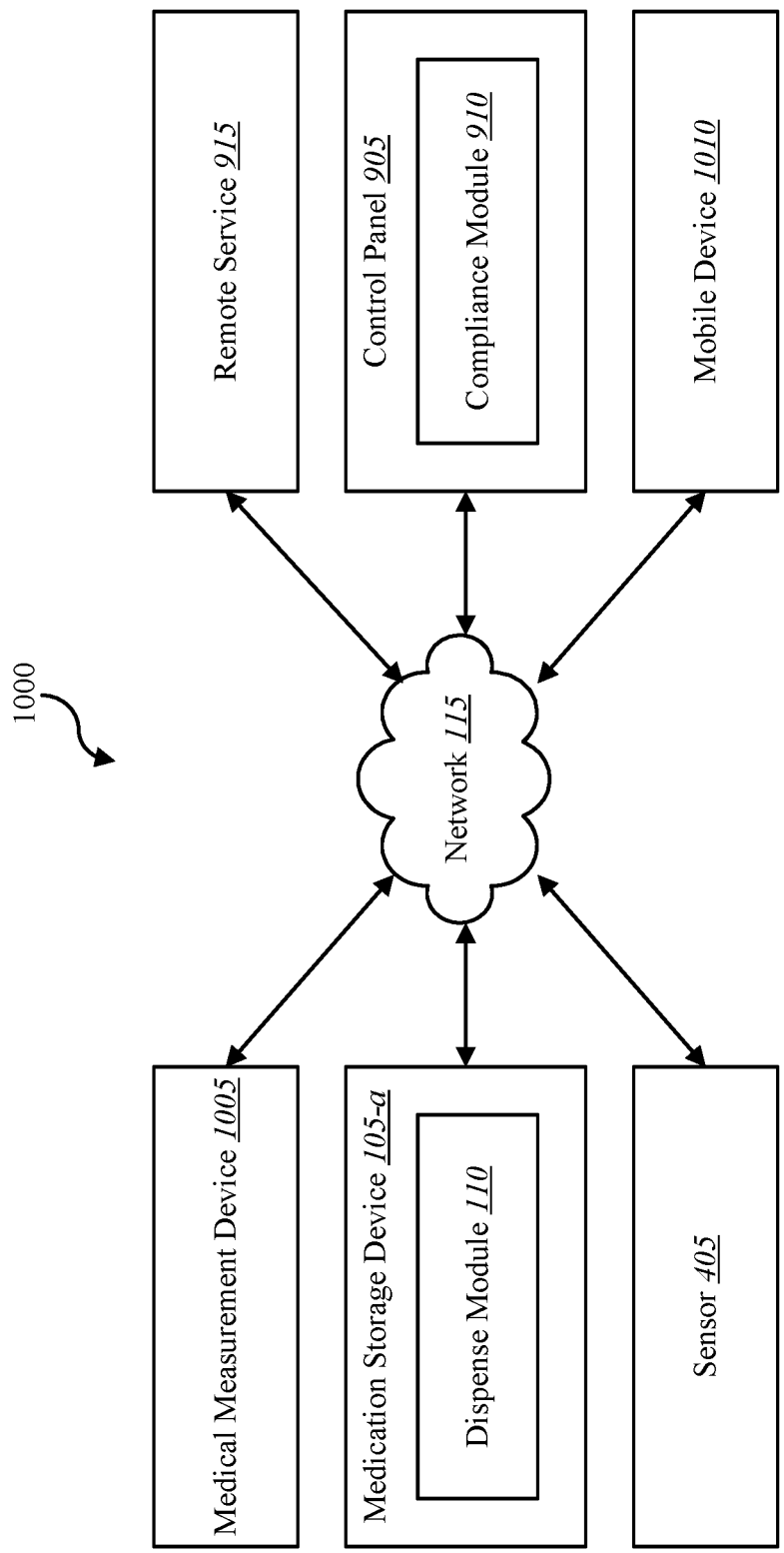
FIG. 10 is a block diagram of another environment in which the present systems and methods may be implemented.

FIG. 10 is a block diagram illustrating another embodiment of environment 1000 in which the present systems and methods may be implemented. Environment 1000 may include at least some of the components of environment 900 described above. Environment 1000 may include, in addition to control panel 905, compliance module 910, and remote service 915, the medication storage device 105-*a* and dispense module 110 described above with reference to FIG. 2, sensor 405 described above with reference to FIG. 4, a medical measurement device 1005, and a mobile device 1010. The components of environment 1000 may communicate via network 115.

The instructions sent from remote service 915 to compliance module 910 may take many different forms. For example, the instructions may be in the form of a request for information, instructions about how to perform a specific activity and/or the frequency of performing the activity, a reminder about consuming a particular medication, or some other request, reminder, description or message. In some examples, remote service 915 may provide instructions in the form of a schedule for when notices should be conveyed to the patient. Compliance module 910 may execute the instructions by generating and/or providing the notices to the patient according to the schedule. The feedback received by compliance module 910 may relate to the entire schedule or particular messages or notices generated in accordance with the schedule. Compliance module 910 may operate to consolidate a plurality of feedbacks or in some way process or manipulate the feedback information prior to communicating the feedback, or a version thereof (e.g., in the form of a summary, average, or the like), to remote service 915 or before generating a non-compliance notice.

Compliance module 910 may operate to communicate directly with any of the medication storage device 105-a, dispense module 110, sensor 405, medical measurement device 1005, and mobile device 1010, in addition to control panel 905. Compliance module 910 may facilitate two-way communication with any of the components of environment 1000. In some embodiments, any one of the components may periodically reach out to compliance module 910 to obtain any or all current instructions in place of or in addition to compliance module 910 actively transmitting the instructions or other information from remote service 915. Similarly, the components of environment 1000 may automatically transmit feedback to compliance module 910 in response to the instructions. Additionally, or alternatively, compliance module 910 may actively reach out to and obtain feedback from any of the components of environment 1000 (e.g., on a periodic basis or after a certain amount of time from when the instructions are sent to or otherwise received by the components of environment 1000).

Any of the features and functionality of medication storage device 105-a and dispense module 110 described above with reference to FIGS. 1-8 may be adapted for use with environment 1000, and in particular cooperating with compliance module 910. For example, dispense module 110 may provide feedback to compliance module 910 any time that medication storage device 105-a is accessed, medication is dispensed by medication storage device 105-a, and/or a particular person accesses or is determined to be in close proximity to medication storage device 105-a. Unauthorized use of medication storage device 105-a may also be conveyed to compliance module 910. A failure to receive feedback from dispense module 110 related to dispensing of medication in accordance with instructions for a patient to consume certain medications may be used by compliance module 910 as a basis for generating a non-compliance notice or alarm.

Sensor 405 may provide feedback related to many different types of instructions, whether in a medical context or other application. For example, sensor 405, as described above, may provide motion detection, which may indicate certain activities of a patient in a certain area of the home (e.g., taking a shower, operating a treadmill, going to bed, or the like). Sensor 405 may also cooperate with medical measurement device 1005 to obtain information about the patient such as a heart rate, body temperature, blood pressure, and the like. Sensor 405 may assist in confirming whether the patient is located on the property, which may be helpful input for compliance module 910 as part of determining how to convey the instructions to the patient (e.g., displaying on control panel 905 versus sending to mobile device 1010 carried by the patient). Sensor 405 may also provide feedback related to activities that are not permitted or are otherwise discouraged for the patient for any number of reasons. The feedback from sensor 405 may provide additional information for medical personnel as part of determining future instructions or compliance with ongoing instructions, messages, recommendations, and the like.

Compliance module 910 may send instructions directly to medical measuring device 1005 to obtain measurements related to the patient. Medical measuring device 1005 may provide the measurements as feedback to compliance module 910. In some embodiments, medical measurement device 1005 is disconnected from network 115. For example, medical measurement device 1005 may be a completely mechanical device without electronics. The patient or caregiver of a patient may use medical measurement device 1005 to obtain information related to the patient and/or the patient's activities and then manually enter the information obtained from medical measurement device 1005 separately as feedback to compliance module 910 (e.g., via a user interface of control panel 905). In one example, compliance module 910 presents a question to the patient (e.g., via control panel 905) such as "is your blood sugar level below X amount?" The patient may use medical measurement device 1005 to obtain his/her blood sugar level and then respond to the proposed question by checking a box (e.g., activating a discreet area of a touch screen) or operating a button of a user interface of control panel 905 with a yes or no response or the blood sugar level.

Mobile device 1010 may be carried by, for example, the patient, a caregiver of the patient, the medical personnel who interfaces with remote service 915 to generate instructions, emergency personnel, or other interested parties. Mobile device 1010 may be used to control or otherwise operate remote service 915. Alternatively, mobile device 1010 may be used to receive alarms or notices related to non-compliance of instructions conveyed to a patient or caregiver via compliance module 910. Mobile device 1010 may be carried by the patient and may be used to communicate instructions to the patient and/or facilitate sending feedback to compliance module 910 in response to instructions. Any of medication storage device 105-a, sensor 405, dispense module 110, and medical measurement device 1005 may communicate directly with mobile device 1010 and/or use mobile device 1010 as a medium for conveying feedback to compliance module 910.

Figure 11:
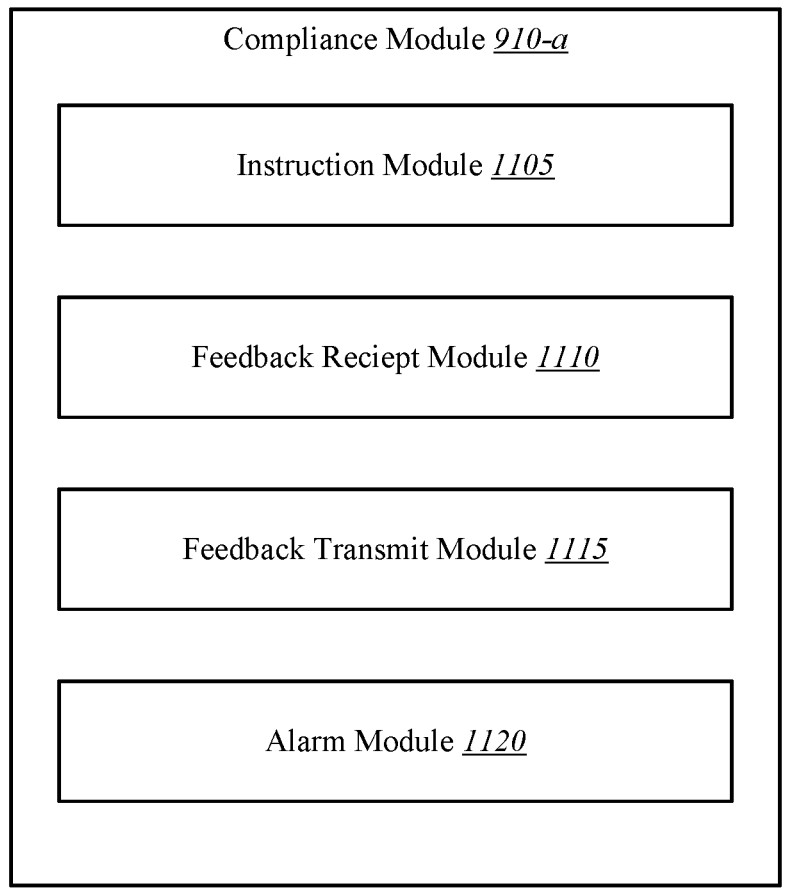
FIG. 11 is a block diagram of a compliance module of the environments shown in FIGS. 9-10.

FIG. 11 is a block diagram illustrating an example compliance module 910-a. Compliance module 910-a may be one example of the compliance module 910 described above with reference to FIGS. 9 and 10. Compliance module 910-a may include an instruction module 1105, a feedback receipt module 1110, a feedback transmit module 1115, and an alarm module 1120. In other examples, compliance module 910-a may include more or fewer of the modules shown in FIG. 11.

Instruction module 1105 may operate to receive instructions from a third party via a service such as the remote service 915 described with reference to FIGS. 9 and 10. Instruction module 1105 may determine how the instructions are conveyed locally such as directly to a control panel, a remote device, a medication storage device, medical measurement device, a sensor, or the like (e.g., see description above related to FIG. 10). Instruction module 1105 may process the instructions and determine a schedule for disseminating the instructions, reconfigure the instructions according to the medium to which the instructions are sent, and/or perform other tasks in response to the instructions. The instructions may include, as described above, inquiries, commands, descriptions, schedules, alternative options, and the like. Instruction module 1105 may both receive instructions and send instructions. At least some of the received instructions may be received locally, while other of the instructions may be received from a remote source. The instructions may be delivered from instruction module 1105 locally or remotely depending on, for example, a determined location of the patient, the type of activity or task that must be completed in view of the instructions, and the like.

Feedback receipt module 1110 is operable to receive feedback from a number of sources including, for example, manually entered feedback from the patient or other person in response to the instructions, a device, sensor or system that operates in response to the instructions, whether instructions are received directly or indirectly. Feedback receipt module 1110 may transform the feedback into a format that addresses the instructions received by instruction module 1105 and/or disseminated by instruction module 1105. In at least one example, feedback receipt module 1110 receives feedback via a control panel of the home automation system.

Feedback transmit module 1115 may operate to deliver feedback in response to the instructions (e.g., instructions received from remote service 915). Feedback transmit module 1115 may transmit feedback through various mediums and to different destinations including, for example, a remote hand-held device carried by the patient, a caregiver of the patient, or the medical personnel who generated the instructions, locally to a control panel of the home automation system, or to a back end system or service. Feedback transmit module 1115 may consolidate or summarize feedback prior to transmitting the feedback. For example, feedback transmit module 1115 may transmit feedback at set times of the day and may transmit the feedback in a format that reduces bandwidth requirements for the communication medium being used (e.g., network 115). Feedback transmit module 1115 may, in some embodiments, transmit feedback only when an alarm condition is identified (e.g., non-compliance with instructions within a predetermined time period).

Alarm module 1120 may operate to determine when the feedback, or the lack of feedback, indicates compliance and/or determine using the feedback or lack of feedback that something of concern exists related to the patient. Alarm module 1120 may communicate the alarm to various destinations including, for example, caregivers of the patient, medical personnel, emergency personnel, a remote service, a remote hand-held device, or the like. The alarm generated and transmitted by alarm module 1120 may be sent to the patient as an urgent reminder or as notice of imminent danger to the patient's health or condition.

Compliance module 910-*a* may, in some embodiments, be used as an incentive program or include capability to monitor activities of one or more persons for purposes of an incentive program. Compliance module 910-*a* may provide a comparison of compliance by a plurality of patients so that the patients can compare their status to similarly situated patients. This comparative data may be displayed, for example, on a control panel of the home automation system, a remote hand-held device of the patient, or the like. The instructions or messages conveyed via instruction module 1105 may convey the comparative information and/or include specific information about how the patient can modify his/her behavior to improve compliance relative to others.

Figure 12:
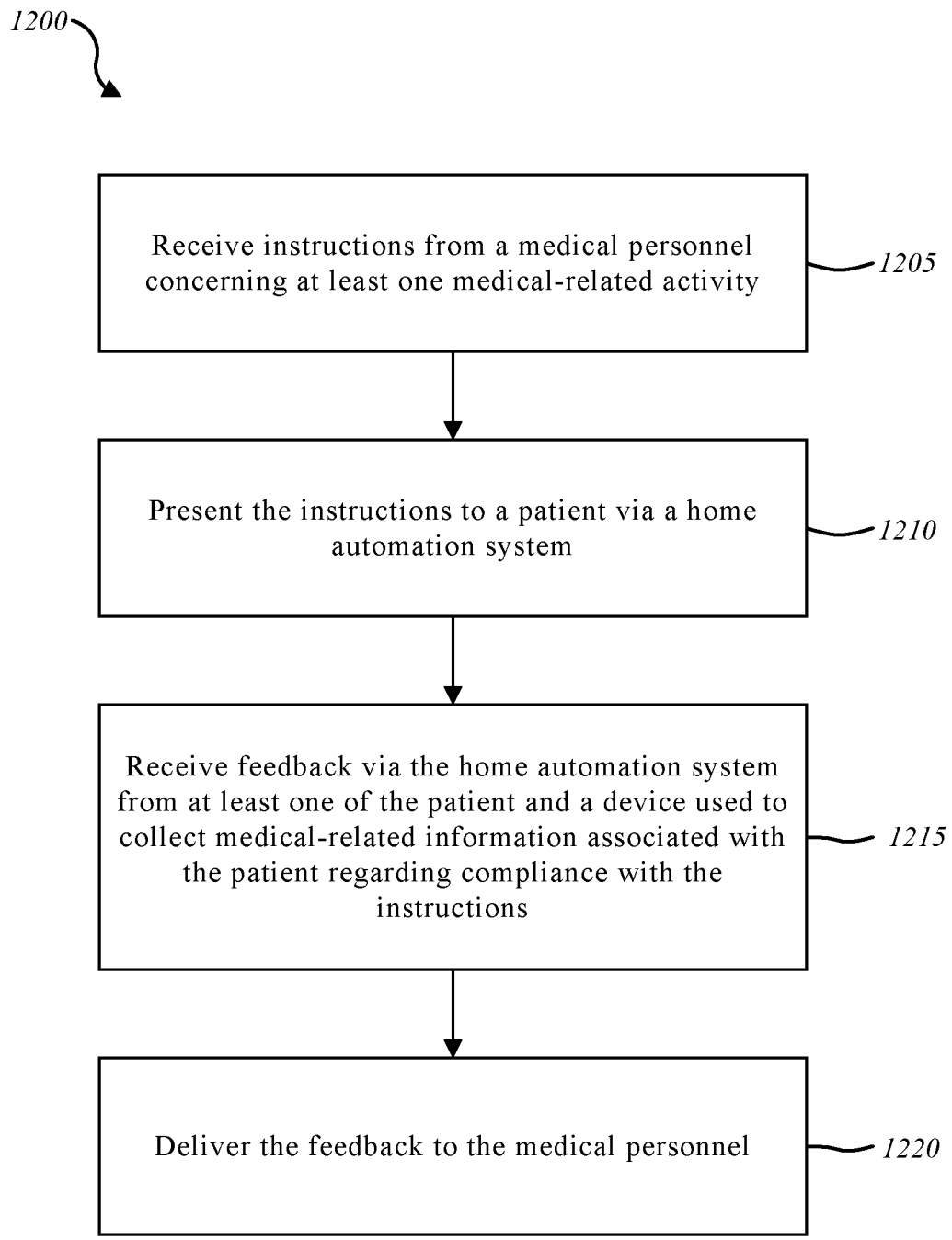
FIG. 12 is a flow diagram illustrating a method for monitoring medical compliance using a home automation system.

FIG. 12 is a flow diagram illustrating one embodiment of a method 1200 for monitoring medical compliance using a home automation system. In some configurations, the method 1200 may be implemented by the compliance module 910 shown and described with reference to FIGS. 9-11. In other examples, the method 1200 may be performed generally by control panel 905 shown in FIGS. 9 and 10, or even more generally by environments 900, 1000 shown in FIGS. 9 and 10.

At block 1205, the method 1200 includes receiving instructions from a medical personnel concerning at least one medical-related activity. Block 1210 includes presenting the instructions to a patient via a home automation system. Block 1215 includes receiving feedback via the home automation system from at least one of the patient and a device used to collect medical-related information associated with the patient regarding compliance with the instructions. Block 1220 includes delivering the feedback to the medical personnel.

The instructions of method 1200 may relate to consumption of medication, and the device may be a medication dispensing device, wherein the feedback includes operation of the medication dispensing device to dispense medication for consumption by the patient. Presenting the instructions may include at least one of displaying a text message or generating an audio message at a control panel of the home automation system. Receiving feedback may include receiving an entry from the patient at a control panel of the home automation system. The entry may include at least one of confirmation of a medication consumption, a measurement from a medical device, and confirmation of a medical-related activity.

Figure 13:
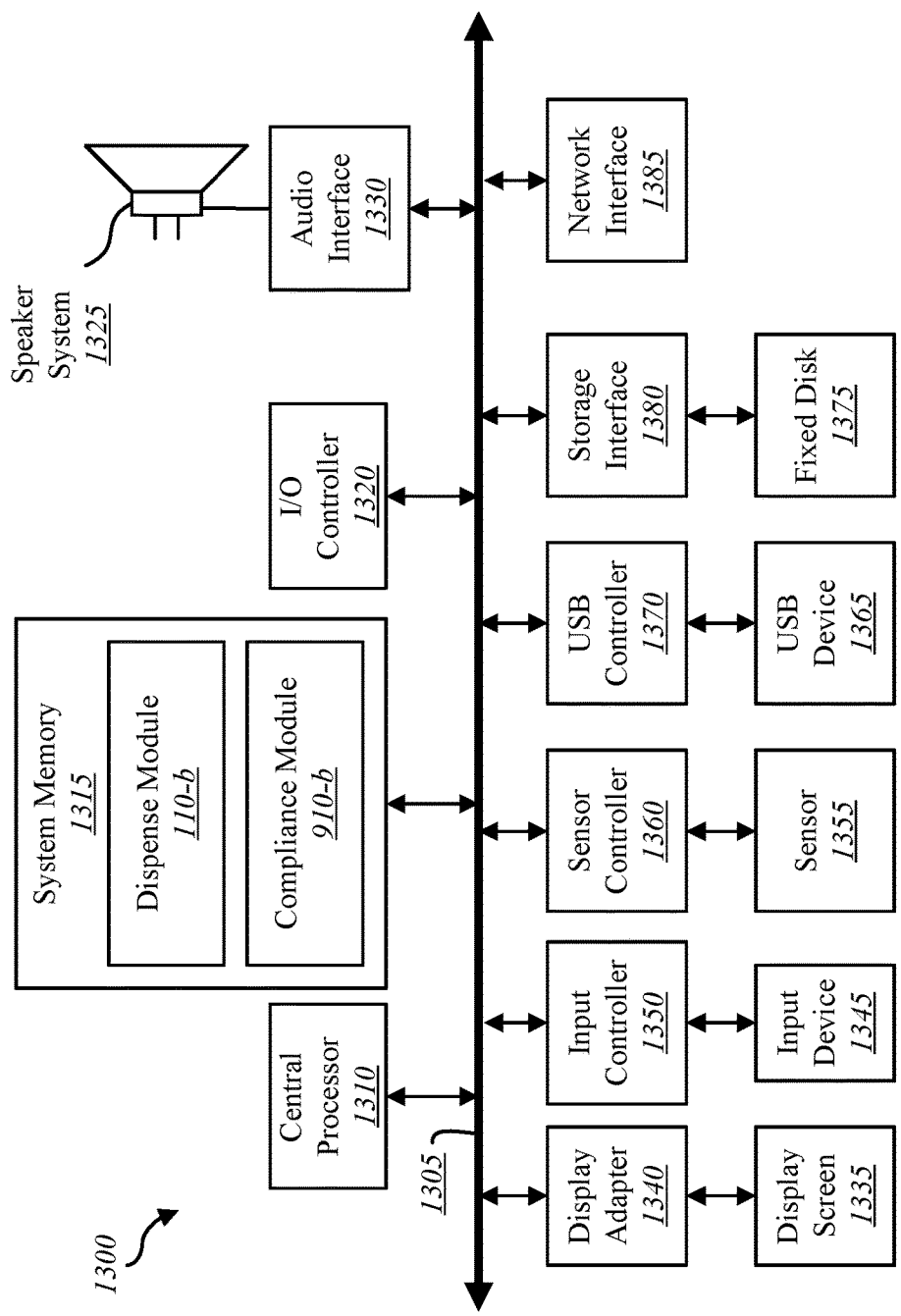
FIG. 13 is a block diagram of a computer system suitable for implementing the present systems and methods of FIGS. 1-12.

FIG. 13 depicts a block diagram of a controller 1300 suitable for implementing the present systems and methods. In one configuration, controller 1300 includes a bus 1305 which interconnects major subsystems of controller 1300, such as a central processor 1310, a system memory 1315 (typically RAM, but which may also include ROM, flash RAM, or the like), an input/output controller 1320, an external audio device, such as a speaker system 1325 via an audio output interface 1330, an external device, such as a display screen 1335 via display adapter 1340, an input device 1345 (e.g., remote control device interfaced with an input controller 1350), multiple USB devices 1365 (interfaced with a USB controller 1370), and a storage interface 1380. Also included are at least one sensor 1355 connected to bus 1305 through a sensor controller 1360 and a network interface 1385 (coupled directly to bus 1305).

Bus 1305 allows data communication between central processor 1310 and system memory 1315, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, a dispense module 110-*b* to implement the present systems and methods may be stored within the system memory 1315. Additionally, or alternatively, the compliance module 910-*b* of FIGS. 9-11 may be stored within the system memory 1315. Applications resident with controller 1300 are generally stored on and accessed via a non-transitory computer readable medium, such as a hard disk drive (e.g., fixed disk drive 1375) or other storage medium. Additionally, applications can be in the form of electronic signals modulated in accordance with the application and data communication technology when accessed via network interface 1385.

Storage interface 1380, as with the other storage interfaces of controller 1300, can connect to a standard computer readable medium for storage and/or retrieval of information, such as a fixed disk drive 1375. Fixed disk drive 1375 may be a part of controller 1300 or may be separate and accessed through other interface systems. Network interface 1385 may provide a direct connection to a remote server via a direct network link to the Internet via a POP (point of presence). Network interface 1385 may provide such connection using wireless techniques, including digital cellular telephone connection, Cellular Digital Packet Data (CDPD) connection, digital satellite data connection, or the like. In some embodiments, one or more sensors (e.g., motion sensor, smoke sensor, glass break sensor, door sensor, window sensor, carbon monoxide sensor, and the like) connect to controller 1300 wirelessly via network interface 1385.

Many other devices or subsystems (not shown) may be connected in a similar manner (e.g., entertainment system, computing device, remote cameras, wireless key fob, wall mounted user interface device, cell radio module, battery, alarm siren, door lock, lighting system, thermostat, home appliance monitor, utility equipment monitor, and so on). Conversely, all of the devices shown in FIG. 13 need not be present to practice the present systems and methods. The devices and subsystems can be interconnected in different ways from that shown in FIG. 13. The aspect of some operations of a system such as that shown in FIG. 13 are readily known in the art and are not discussed in detail in this application. Code to implement the present disclosure can be stored in a non-transitory computer-readable medium such as one or more of system memory 1315 or fixed disk drive 1375. The operating system provided on controller 1300 may be iOS®, ANDROID®, MS-DOS®, MS-WINDOWS®, OS/2®, UNIX®, LINUX®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered exemplary in nature since many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

Furthermore, while various embodiments have been described and/or illustrated herein in the context of fully functional computing systems, one or more of these exemplary embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the exemplary embodiments disclosed herein.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. An apparatus for dispensing medication, comprising:
   a processor;
   memory in electronic communication with the processor, and
   instructions stored in the memory and executable by the processor to cause the apparatus to:
      receive information of a person from a device carried by an authorized user indicating a proximity of the authorized user to the apparatus;
      determine whether the person is attempting to access a compartment of the apparatus casing the medication based at least in part on sensor data;
      determine a time period of the received information of the person based at least in part on the person attempting to access the compartment of the apparatus casing the medication;
      determine that the time period satisfies a threshold timeframe when the medication is to be taken by the person based at least in part on a behavioral pattern of the person; and
      permit the authorized user to dispense the medication after receiving the information and based at least in part on the time period satisfying the threshold timeframe.

2. The apparatus of claim 1, wherein the instructions are executable by the processor to:
receive positioning information from the device carried by the authorized user, wherein the device is a portable electronic device wearable by the person and wherein the instructions to receive the information are further executable by the processor to receive the positioning information.

3. The apparatus of claim 2, wherein the instructions are executable by the processor to:
determine a distance between the person and the apparatus based at least in part on the positioning information; and
determine whether the distance is within a threshold of the apparatus, wherein the instructions to dispense the medication are further executable by the processor based at least in part on the distance being within the threshold of the apparatus.

4. The apparatus of claim 2, wherein the portable electronic device comprises at least one of a pendent, a bracelet, or an anklet, or a combination thereof.

5. The apparatus of claim 1, wherein the instructions are executable by the processor to:
receive authentication information from a portable electronic device wearable by the person, the authentication information comprises at least one of a voice command, a fingerprint, or facial recognition data, or a combination thereof, wherein the instructions to receive the information are further executable by the processor to receive the authentication information; and
confirm an identification of the person based at least in part on the authentication information, wherein the instructions to dispense the medication are further executable by the processor based at least in part on the confirmation.

6. The apparatus of claim 1, wherein the instructions are executable by the processor to:
compare the received information of the person to medication-related information of the medication, the received information comprising at least one of a blood pressure of the person, a temperature of the person, a glucose level of the person, a weight of the person, or a combination thereof, wherein the instructions to dispense the medication are further executable by the processor based at least in part on the comparison.

7. The apparatus of claim 6, wherein the medication-related information comprises at least one of a frequency of dispensing the medication, an amount of the medication for dispensing, a timeframe for dispensing the medication, or a combination thereof.

8. A method for dispensing medication, comprising:
receiving information of a person from a device carried by an authorized user indicating a proximity of the authorized user to a medication dispenser;
determining whether the person is attempting to access a compartment of an apparatus casing the medication based at least in part on sensor data;
determining a time period of the received information of the person based at least in part on the person attempting to access the compartment of the apparatus casing the medication;
determining that the time period satisfies a threshold timeframe when the medication is to be taken by the person based at least in part on a behavioral pattern of the person; and
permitting the authorized user to access, from the medication dispenser, the medication after receiving the information and based at least in part on the time period satisfying the threshold timeframe.

9. The method of claim 8, further comprising:
receiving positioning information from the device carried by the authorized user, wherein the device is a portable electronic device wearable by the person and wherein receiving the information further comprises receiving the positioning information;
determining a distance between the person and the medication dispenser based at least in part on the positioning information; and
determining whether the distance is within a threshold of the medication dispenser, wherein providing the medication is further based at least in part on the distance being within the threshold of the medication dispenser.

10. The method of claim 8, further comprising:
receiving authentication information from a portable electronic device wearable by the person, the authentication information comprising at least one of a voice command, a fingerprint, or facial recognition data, or a combination thereof, wherein receiving the information further comprises receiving the authentication information; and
confirming an identification of the person based at least in part on the authentication information, wherein providing the medication is further based at least in part on the confirmation.

11. A non-transitory computer-readable medium storing code for dispensing medication, the code comprising instructions executable by a processor to:
receive information of a person from a device carried by an authorized user indicating a proximity of the authorized user to a medication dispenser;
determine whether the person is attempting to access a compartment of an apparatus casing the medication based at least in part on sensor data;
determine a time period of the received information of the person based at least in part on the person attempting to access the compartment of the apparatus casing the medication;
determine that the time period satisfies a threshold timeframe when the medication is to be taken by the person based at least in part on a behavioral pattern of the person; and
permit the authorized user to access, from the medication dispenser, a medication after receiving the information and based at least in part on the time period satisfying the threshold timeframe.

12. The non-transitory computer-readable medium of claim 11, wherein the instructions are further executable by the processor to:
receive positioning information from the device carried by the authorized user, wherein the device is a portable electronic device wearable by the person and wherein the instructions to receive the information are further executable by the processor to receive the positioning information;
determine a distance between the person and the medication dispenser based at least in part on the positioning information; and
determine whether the distance is within a threshold of the medication dispenser, wherein the instructions to provide the medication are further executable by the processor based at least in part on the distance being within the threshold of the medication dispenser.

13. The non-transitory computer-readable medium of claim 11, wherein the instructions are further executable by the processor to:
- receive authentication information from a portable electronic device wearable by the person, the authentication information comprising at least one of a voice command, a fingerprint, or facial recognition data, or a combination thereof, wherein the instructions to receive the information are further executable by the processor to receive the authentication information; and
- confirm an identification of the person based at least in part on the authentication information, wherein the instructions to provide the medication are further executable by the processor based at least in part on the confirmation.

* * * * *